United States Patent
Huboux et al.

(10) Patent No.: US 11,174,249 B2
(45) Date of Patent: Nov. 16, 2021

(54) COOLING COMPOSITION

(71) Applicant: FIRMENICH SA, Meyrin (CH)

(72) Inventors: Alexandre Huboux, Meyrin (CH); Wolfgang Fieber, Meyrin (CH); Pascal Beaussoubre, Meyrin (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/630,889

(22) PCT Filed: Jul. 12, 2018

(86) PCT No.: PCT/EP2018/069017
§ 371 (c)(1),
(2) Date: Jan. 14, 2020

(87) PCT Pub. No.: WO2019/012071
PCT Pub. Date: Jan. 17, 2019

(65) Prior Publication Data
US 2020/0157083 A1 May 21, 2020

(30) Foreign Application Priority Data

Jul. 14, 2017 (EP) ..................................... 17181445
Dec. 22, 2017 (DE) ......................... 202017107872.8
Mar. 28, 2018 (EP) ..................................... 18164604

(51) Int. Cl.
C07D 409/12 (2006.01)
A23L 27/20 (2016.01)
A61K 8/49 (2006.01)
A61Q 13/00 (2006.01)

(52) U.S. Cl.
CPC ........ C07D 409/12 (2013.01); A23L 27/2054 (2016.08); A61K 8/4986 (2013.01); A61Q 13/00 (2013.01); A61K 2800/244 (2013.01); C07B 2200/13 (2013.01)

(58) Field of Classification Search
CPC .................................................. C07D 409/12
See application file for complete search history.

(56) References Cited

U.S. PATENT DOCUMENTS

| 4,396,670 A | 8/1983 | Sinclair |
| 2017/0087199 A1 | 3/2017 | Patron et al. |
| 2017/0096418 A1* | 4/2017 | Patron ..................... A23L 33/10 |

FOREIGN PATENT DOCUMENTS

| WO | 0141915 A1 | 6/2001 |
| WO | 2012061698 A2 | 5/2012 |
| WO | 2014090293 A1 | 6/2014 |
| WO | 2017058594 A1 | 4/2017 |

OTHER PUBLICATIONS

Bône et al., "Microencapsulated Fragrances in Melamine Formaldehyde Resins", Chimia, Published 2011, pp. 177-181, vol. 65, No. 3.
Cohen et al., "GRAS 27 Flavoring Substances", Food Technology Magazine, Published Aug. 1, 2015, pp. 40-59, vol. 69, No. 8.
Dietrich et al., "Amino Resin Microcapsules", Acta Polymerica, Published 1989, pp. 243-251, vol. 40, No. 4.
Dietrich et al., "Amino Resin Microcapsules", Acta Polymerica, Published 1989, pp. 325-331, vol. 40, No. 5.
Dietrich et al., "Amino Resin Microcapsules", Acta Polymerica, Published 1989, pp. 683-690, vol. 40, No. 11.
Dietrich et al., "Amino Resin Microcapsules", Acta Polymerica, Published 1990, pp. 91-95, vol. 41, No. 2.
Lee et al., "Microencapsulation of fragrant oil via in situ polymerization: effects of pH and melamine-formaldehyde molar ratio", Journal of Microencapsulation, Published 2002, pp. 559-569, vol. 19, No. 5.
International Search Report and Written Opinion for International Application No. PCT/EP2018/069017, dated Sep. 10, 2018, 19 pages.

* cited by examiner

Primary Examiner — Shawquia Jackson
(74) Attorney, Agent, or Firm — Armstrong Teasdale LLP

(57) ABSTRACT

Described herein is a composition of matter comprising i) at least one compound of formula (I)

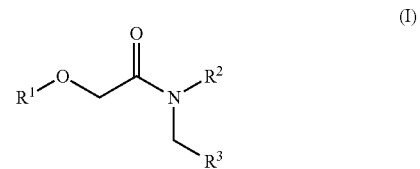

in the form of any of its stereoisomers; and wherein $R^1$ represents a phenyl group optionally substituted by one or two $C_{1-3}$ alkyl or alkoxy groups or by one or two halides group; $R^2$ and $R^3$ represent, independently from each other a heterocyclic group comprising from 1 to 3 heteroatoms selected from nitrogen, oxygen and sulfur, optionally substituted by one or two $C_{1-3}$ alkyl groups; and ii) at least a $C_{1-6}$ linear or branched alkyl lactate.

Also described herein is a method of using the composition of matter as part of a flavoring or perfuming composition or of a flavoring or perfuming consumer product. Also described herein is a process to prepare the composition of matter and the polymorph of compound of formula (I).

30 Claims, 1 Drawing Sheet

δ (ppm)

° 2 theta (Cu K-alpha radiation)

COOLING COMPOSITION

CROSS-REFERENCE TO RELATED APPLICATIONS

The present application is a U.S. National Application of PCT/EP2018/069017, filed on Jul. 12, 2018, which claims the benefit of priority to European Patent Application Serial No. 17181445.2, filed on Jul. 14, 2017, European Patent Application Serial No. 18164604.3, filed on Mar. 28, 2018, and German Utility Model Serial No. 202017107872.8, filed on Dec. 22, 2017, the entire contents of which are hereby incorporated by reference.

TECHNICAL FIELD

The present invention relates to the field of flavor or perfumery. More particularly, it concerns a composition of matter comprising at least one compound of formula (I) and at least a $C_{1-6}$ linear or branched alkyl lactate and the use of said composition of matter in a flavor or perfumery composition. Therefore, following what is mentioned herein, the present invention comprises the invention's composition of matter as part of a flavoring or perfuming composition or of a flavoring or perfuming consumer product. The process to prepare the invention's composition of matter and the polymorph of compound of formula (I), in particular of N-(1H-pyrazol-3-yl)-N-(thiophen-2-ylmethyl)-2-(p-tolyloxy)acetamide, are also an object of the invention.

PRIOR ART

One of the most sought ingredients in the perfumery and flavor field are the ones imparting a cold or a cooling impression providing to the consumer product a freshness and a cleanness sensation which is used in a multitude of perfumed and flavored consumer products. Since decades, a lot of efforts have been put in place in order to obtain compounds possessing this effect.

In this respect, very powerful novel cooling substances have been reported in WO 2012/061698 and in WO 2017/058594 which are modulators of transient receptor potential channel melastin member 8 (TRPM8), a channel involved in particular with cooling sensation. These compounds are particularly efficient and provide cooling effect at very low concentration. Actually, the cooling effect is observed with only trace amount of this powder. However, said compounds, at room temperature and under atmospheric pressure, are in a form of a very fine powder. Due to the strength of these compounds, they should be diluted in a solvent, in particular in a solvent authorized in flavored consumer product. However said compounds possess a low solubility in the most common flavor solvents.

So there is a need to solubilize these compounds in order to provide these compounds in a diluted form. The present invention provides a solution to the above-mentioned problem by using alkyl lactates.

SUMMARY OF THE INVENTION

The invention relates to a novel composition comprising at least one compound of formula (I) and at least a $C_{1-6}$ linear or branched alkyl lactate which allows facilitating the use and the handling of the compound of formula (I).

So, a first object of the present invention is a composition of matter comprising i) at least one compound of formula (I)

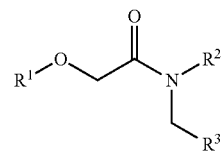

in the form of any of its stereoisomers; and wherein $R^1$ represents a phenyl group optionally substituted by one or two $C_{1-3}$ alkyl or alkoxy groups or by one or two halides group; $R^2$ and $R^3$ represent, independently from each other a heterocyclic group comprising from 1 to 3 heteroatoms selected from nitrogen, oxygen and sulfur, optionally substituted by one or two $C_{1-3}$ alkyl groups; and ii) at least a $C_{1-6}$ linear or branched alkyl lactate.

A second object of the present invention is a flavoring composition comprising:
i) at least a composition of matter comprising at least one compound of formula (I) and at least a $C_{1-6}$ linear or branched alkyl lactate;
ii) at least one ingredient selected from the group consisting of a flavor carrier, a flavoring co-ingredient and a mixture thereof; and
iii) optionally at least one flavor adjuvant.

A third object of the present invention is flavored consumer product comprising a composition of matter as defined above or a flavoring composition as defined above.

Another object of the invention is a perfuming composition comprising:
i) at least a composition of matter comprising at least one compound of formula (I) and at least a $C_{1-6}$ linear or branched alkyl lactate;
ii) at least one ingredient selected from the group consisting of a perfumery carrier, a perfuming co-ingredient and a mixture thereof; and
iii) optionally at least one perfumery adjuvant.

Another object of the invention is a perfumed consumer product comprising a composition of matter as defined above or a perfuming composition as defined above.

Another object of the invention is a method to confer, enhance, improve or modify the taste properties of a flavoring composition or of a flavored article or of a surface, which method comprises adding to said composition or article an effective amount of the invention's composition of matter, e.g. to impart its typical note.

Another object of the invention is a method to confer, enhance, improve or modify the odor properties of a perfuming composition or of a perfumed article or of a surface, which method comprises adding to said composition or article an effective amount of the composition of matter as defined above.

Another object of the invention is a process for preparing the composition of matter as defined above comprising the step of
a) preparing compound of formula (I) as defined in claim 1 by reacting a compound of formula

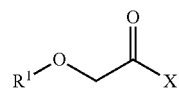

wherein R¹ represents a phenyl group optionally substituted by one or two $C_{1-3}$ alkyl or alkoxy groups or by one or two halide groups; and X represents a hydroxyl group, a $C_{1-10}$ alkoxy group or a chloride atom;
with a compound of formula

(III)

wherein R² and R³ represent, independently from each other a heterocyclic group comprising from 1 to 3 heteroatoms selected from nitrogen, oxygen and sulfur optionally substituted by one or two $C_{1-3}$ alkyl groups;
b) crystallizing the reaction mixture obtained in step a);
c) filtering the solution of the crystallized product obtained in step b);
d) drying the crystallized product obtained in step c); and
e) solubilizing the dried crystallized product obtained in step d) in a $C_{1-6}$ linear or branched alkyl lactate.

A last object of the invention is a crystalline form of N-(1H-pyrazol-3-yl)-N-(thiophen-2-ylmethyl)-2-(p-tolyloxy)acetamide characterized by main peaks in its powder X-ray diffraction pattern obtained using copper K-alpha, radiation at 6.86, 12.46, 15.87, 17.38, 17.70, 17.93, 18.43, 19.46, 20.61, 22.08, 23.03, 23.43, 24.36, 26.11, 27.59, 34.68.

DESCRIPTION OF THE INVENTION

Figure 1:
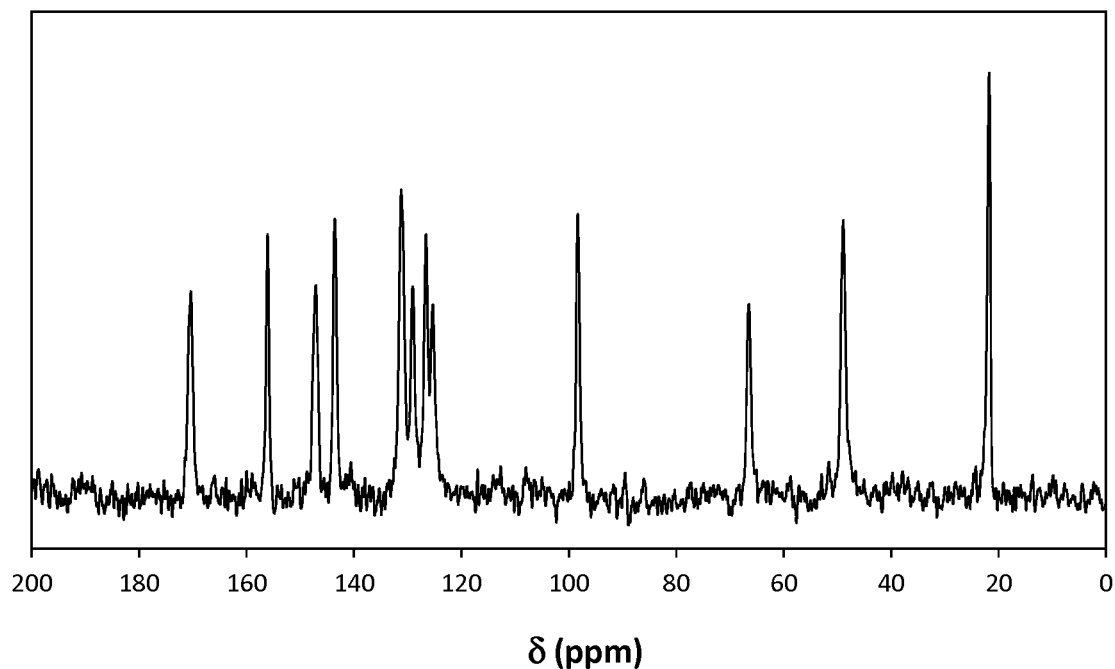
FIG. 1 represents the 13C Solid state NMR spectrum obtained as mentioned in example 3.
Figure 2:
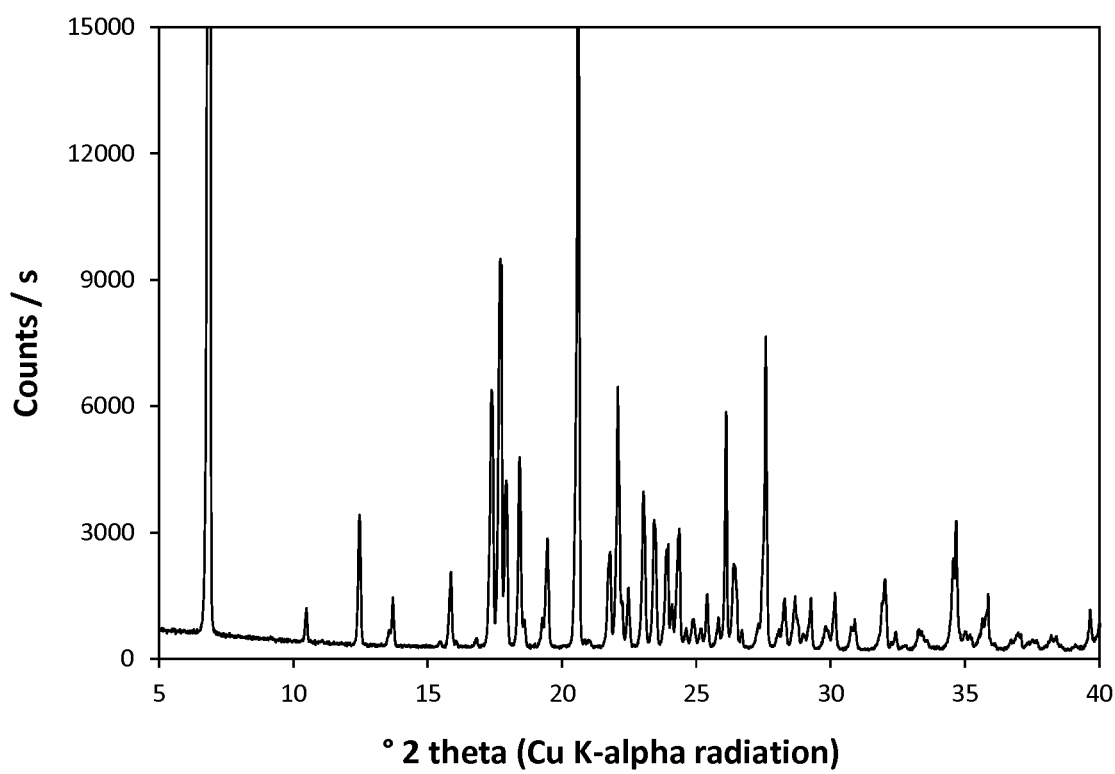
FIG. 2 represents X-Ray Powder diffraction spectrum obtained as mentioned in example 3.

Surprisingly, it has now been discovered that compounds of formula (I) could be easily solubilized in $C_{1-6}$ linear or branched alkyl lactate which allows using said compounds at a very low level while alleviating the handling of these compounds in their solid form.

Therefore, a first object of the invention is a composition of matter comprising
i) at least one compound of formula (I)

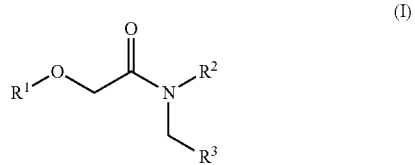

(I)

in the form of any one of its stereoisomers; and wherein R¹ represents a phenyl group optionally substituted by one or two $C_{1-3}$ alkyl or alkoxy groups or by one or two halide groups; R² and R³ represent, independently from each other a heterocyclic group comprising from 1 to 3 heteroatoms selected from nitrogen, oxygen and sulfur, optionally substituted by one or two $C_{1-3}$ alkyl groups; and
ii) at least a $C_{1-6}$ linear or branched alkyl lactate.

For the sake of clarity, by the expression "any one of its stereoisomers", or the similar, it is meant the normal meaning understood by a person skilled in the art, i.e. that the compound of formula (I) is in the form of any diastereomer, enantiomer or mixture thereof. In other words, compound of formula (I) have an amide functional group which could be cis or trans or a mixture thereof. Furthermore, the compound of formula (I) may additionally have at least one stereogenic center which can have different stereochemistry (i.e. when one stereogenic center is present, compound (I) can have (R) or (S) configuration). Each of said stereogenic centers can be in a relative configuration R or S or a mixture thereof. Said compound of formula (I) can be in a form of pure enantiomer or diastereoisomer, or in a form of a mixture of stereoisomers.

According to any one of the above embodiments, R¹ represents a phenyl group optionally substituted by one or two $C_{1-3}$ alkyl or alkoxy groups or by one or two halide groups. Preferably, R¹ represents a phenyl group substituted by one or two $C_{1-3}$ alkyl or alkoxy groups or by one or two halide atoms. Preferably, R¹ represents a phenyl group substituted by one or two $C_{1-2}$ alkyl or alkoxy group or by one or two fluoro groups. Even more preferably, R¹ represents a phenyl group substituted by one or two methyl, ethyl, methoxy groups or by one fluoro group. The substituents to the phenyl group may be in ortho and/or meta and/or para position relative to the bond between the oxygen atom and R¹ group. Preferably, R¹ may be selected from the group consisting of para-tolyl, 4-ethylphenyl, 4-methoxyphenyl, 4-fluorophenyl, 3,4-dimethylphenyl and meta-tolyl. Even more preferably, R¹ may be para-tolyl or 4-ethylphenyl. Even more preferably, R¹ may be para-tolyl.

By the term "ortho", "meta" and "para", it is meant the normal meaning in the art; i.e. the ortho position corresponds to two substituents of the phenyl group occupying positions next to each other; the meta position corresponds to two substituents of the phenyl group occupying positions 1 and 3 and para position corresponds to two substituents of the phenyl group occupying positions 1 and 4.

According to any one of the above embodiments, R² and R³ represent, independently from each other a heterocyclic group comprising from 1 to 3 heteroatoms selected from nitrogen, oxygen and sulfur, optionally substituted by one or two $C_{1-3}$ alkyl groups. Preferably, R² and R³ represent, independently from each other a heterocyclic group comprising from 1 to 3 heteroatoms selected from nitrogen, oxygen and sulfur. Even more preferably, R² and R³ represent, independently from each other a heterocyclic group comprising from 1 to 3 heteroatoms selected from nitrogen and sulfur.

According to any one of the above embodiments, R² represents a heterocyclic group comprising from one or two nitrogen atoms. Preferably, R² represents a pyrazolyl group.

According to any one of the above embodiments, R³ represents a heterocyclic group comprising from one or two sulfur atoms. Preferably, R³ represents a thiophenyl group.

According to any one of the above embodiments, the compound of formula (I) may be selected from the group consisting of N-(1H-pyrazol-3-yl)-N-(thiophen-2-ylmethyl)-2-(p-tolyloxy) acetamide, 2-(4-fluorophenoxy)-N-(1H-pyrazol-3-yl)-N-(thiophen-2-ylmethyl)acetamide, 2-(4-ethylphenoxy)-N-(1H-pyrazol-3-yl)-N-(thiophen-2-ylmethyl)acetamide, 2-(4-methoxyphenoxy)-N-(1H-pyrazol-3-yl)-N-(thiophen-2-ylmethyl)acetamide, N-(1H-pyrazol-3-yl)-N-(thiophen-2-ylmethyl)-2-(m-tolyloxy) acetamide and 2-(3,4-dimethylphenoxy)-N-(1H-pyrazol-3-yl)-N-(thiophen-2-ylmethyl)acetamide. Said compounds possess a pyrazolyl group. It is well known that this group exists under two tautomeric forms; i.e. 1H-pyrazol-3-yl and 1H-pyrazol-5-yl. These two forms equilibrate very rapidly. In other words, when the invention's composition of matter comprises N-(1H-pyrazol-3-yl)-N-(thiophen-2-ylmethyl)-2-(p-tolyloxy)acetamide, inevitably the composition also comprises N-(1H-pyrazol-5-yl)-N-(thiophen-2-ylmethyl)-2-(p-tolyloxy)acetamide. The same applies to the other compounds of above-listed; i.e. 2-(4-fluorophenoxy)-N-(1H-pyrazol-3-yl)-N-(thiophen-2-ylmethyl)acetamide is in equilibrium with 2-(4-fluorophenoxy)-N-(1H-pyrazol-5-yl)-N-(thiophen-2-ylmethyl)acetamide, 2-(4-ethylphenoxy)-N-(1H-pyrazol-3-yl)-N-(thiophen-2-ylmethyl)acetamide is in equilibrium with 2-(4-ethylphenoxy)-N-(1H-pyrazol-5-yl)-N-(thiophen-2-ylmethyl)acetamide, 2-(4-methoxyphenoxy)-N-(1H-pyrazol-3-yl)-N-(thiophen-2-ylmethyl)acetamide is in equilibrium with 2-(4-methoxyphenoxy)-N-(1H-pyrazol-5-yl)-N-(thiophen-2-ylmethyl)acetamide, N-(1H-pyrazol-3-yl)-N-(thiophen-2-ylmethyl)-2-(m-tolyloxy)acetamide is in equilibrium with N-(1H-pyrazol-5-yl)-N-(thiophen-2-ylmethyl)-2-(m-tolyloxy)acetamide and 2-(3,4-dimethylphenoxy)-N-(1H-pyrazol-3-yl)-N-(thiophen-2-ylmethyl)acetamide is in equilibrium with 2-(3,4-dimethylphenoxy)-N-(1H-pyrazol-5-yl)-N-(thiophen-2-ylmethyl)acetamide. Preferably, the compound of formula (I) is N-(1H-pyrazol-3-yl)-N-(thiophen-2-ylmethyl)-2-(p-tolyloxy)acetamide.

According to any one of the above embodiments, the composition of matter comprises a $C_{1-6}$ linear or branched alkyl lactate. Preferably, the composition of matter comprises a $C_{1-4}$ linear or branched alkyl lactate. Even more preferably, the composition of matter comprises a $C_{1-4}$ linear alkyl lactate. Even more preferably, the composition of matter comprises ethyl lactate.

According to any one of the above embodiments, the composition of matter comprises from 0.1 wt % to 20 wt % of at least one compound of formula (I) relative to the total weight of the composition and from 80 wt % to 99.9 wt % of at least a $C_{1-6}$ linear or branched alkyl lactate, relative to the total weight of the composition. Preferably, the composition of matter comprises from 0.5 wt % to 15 wt % of at least one compound of formula (I) relative to the total weight of the composition and from 85 wt % to 99.5 wt % of at least a $C_{1-6}$ linear or branched alkyl lactate, relative to the total weight of the composition. Even more preferably, the composition of matter comprises from 1 wt % to 10 wt % of at least one compound of formula (I) relative to the total weight of the composition and from 90 wt % to 99 wt % of at least a $C_{1-6}$ linear or branched alkyl lactate, relative to the total weight of the composition.

The invention's composition of matter may be used as a flavoring ingredient. The invention concerns the use of a composition of matter comprising at least one compound of formula (I) and at least a $C_{1-6}$ linear or branched alkyl lactate as a flavoring ingredient. In other words, it concerns a method or a process to confer, enhance, improve or modify the taste properties of a flavoring composition or of a flavored article or of a surface, which method comprises adding to said composition or article an effective amount of the invention's composition of matter, e.g. to impart its typical note.

By "use of a composition of matter" it has to be understood here also the use of any composition containing at least one compound of formula (I) and at least a $C_{1-6}$ linear or branched alkyl lactate and which can be advantageously employed in the flavor industry.

By "taste", it meant to designate the taste perception and the taste sensation.

Said compositions, which in fact can be advantageously employed as flavoring ingredients, are also an object of the present invention.

Therefore, another object of the present invention is a flavoring composition comprising:
  i) at least a composition of matter comprising at least one compound of formula (I) and at least a $C_{1-6}$ linear or branched alkyl lactate, as defined above;
  ii) at least one ingredient selected from the group consisting of a flavor carrier, a flavoring co-ingredient and a mixture thereof; and
  iii) optionally at least one flavor adjuvant.

By "flavor carrier", it is meant a material which is substantially neutral from a flavor point of view, insofar as it does not significantly alter the organoleptic properties of flavoring ingredients. The carrier may be a liquid or a solid.

Suitable liquid carriers include, for instance, an emulsifying system, i.e. a solvent and a surfactant system, or a solvent commonly used in flavors. A detailed description of the nature and type of solvents commonly used in flavor cannot be exhaustive. Suitable solvents include, for instance, propylene glycol, triacetine, neobee, triethyl citrate, benzylic alcohol, ethanol, vegetable oils such as Linseed oil, sunflower oil or coconut oil or terpenes.

Suitable solid carriers include, for instance, absorbing gums or polymers, or even encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs-und Gehermittel in Lebensmittel, Band 2 der Schriftenreihe Lebensmittelchemie, Lebensmittelqualitat, Behr's VerlagGmbH & Co., Hamburg, 1996. Encapsulation is a well-known process to a person skilled in the art, and may be performed, for instance, using techniques such as spray-drying, agglomeration, extrusion, coacervation and the like.

By "flavoring co-ingredient" it is meant here a compound, which is used in flavoring preparations or compositions to impart a hedonic effect. In other words such an ingredient, to be considered as being a flavoring one, must be recognized by a person skilled in the art as being able to impart or modify in a positive or pleasant way the taste of a composition, and not just as having a taste. Said flavoring ingredient is not a compound of formula (I).

The nature and type of the flavoring co-ingredients present in the flavoring composition do not warrant a more detailed description here, the skilled person being able to select them on the basis of its general knowledge and according to intended use or application and the desired organoleptic effect. In general terms, these flavoring co-ingredients belong to chemical classes as varied as alcohols, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of flavor. It is also understood that said co-ingredients may also be compounds known to release in a controlled manner various types of flavoring compounds.

In particular, one may cite as flavoring co-ingredients which are commonly used in flavor formulations: essential oils obtained from mint plants, such as, for example, peppermint, spearmint and Japanese peppermint, mint piperita oil and other extracts (Absolute, oleoresin, washed oil), mint piperita rectified India oil and other extracts (Absolute, oleoresin, washed oil), mint spicata native oil and other extracts (Absolute, oleoresin, washed oil), mint spicata US oil and other extracts (Absolute, oleoresin, washed oil), mint arvensis oil and other extracts (Absolute, oleoresin, washed oil), mint cardiaca oil and other extracts (Absolute, oleoresin, washed oil), oil of all mint varieties obtainable from breeding, oil from hybrid mint plant such as the one known as 13-S12-2, 13-39-9, 13-A36-13, 07-A3-11, 09-6-2, 11-A35-3, 07-A3-5A, 14-27-71, 08-6-10, 14-41-16, 08-A20-3, 14-27-89, 05-19-1, *Eucalyptus globulus* oil and other extracts (Absolute, oleoresin, washed oil), eucalyptol, Anethol (natural and synthetic), star anise oil, fennel oil, basil oil, clove oil all types (Bud, Stem, leaves), eugenol, cinnamic aldehyde, cassia oil, cinnamon bark oil, cinnamon leaf oil, cinnamon bud oil, menthol (all grades: L and DL (Racemic)), pine oil (all types and origins), sage oil and other extracts (Absolute, oleoresin, washed oil), chamomile and other extracts (Absolute, oleoresin, washed oil), vanillin (natural and synthetic) and other extracts (Absolute, oleoresin, washed oil), lemon oil all types, orange oil and other extracts (Absolute, oleoresin, washed oil), lime oil and other extracts (Absolute, oleoresin, washed oil), mandarin oil, tangerine oil, maltol, ethyl maltol, furaneol, benzophenone, all lactones, ethyl butyrate, liquorice extracts, (Z)-3-hexenyl acetate, (Z)-3-hexen-1-ol, (E)-2-hexen-1-ol or methyl salicylate. The person skilled in the art is well aware that natural oil could be replaced by synthetic and artificial blends mimicking natural oil sensory profile. Said blends could also be used as a flavor co-ingredient.

By "flavor adjuvant" we mean here an ingredient capable of imparting additional added benefit such as a color, a particular light resistance, chemical stability, and so on. A detailed description of the nature and type of adjuvant commonly used in flavoring compositions cannot be exhaustive. Nevertheless, such adjuvants are well known to a person skilled in the art who will be able to select them on the basis of its general knowledge and according to intended use or application.

A composition consisting of at least one compound of formula (I), at least a $C_{1-6}$ linear or branched alkyl lactate and at least one flavor carrier represents a particular embodiment of the invention as well as a flavoring composition comprising at least one compound of formula (I), at least a $C_{1-6}$ linear or branched alkyl lactate, at least one flavor carrier, at least one flavor co-ingredient, and optionally at least one flavor adjuvant.

According to any one of the above embodiments, the invention's composition may comprise additional at least one cooling agent. Non limited-examples of suitable cooling agent includes WS-23 (2-Isopropyl-N,2,3-trimethylbutyramide), FEMA 3804; WS-3 (N-Ethyl-p-menthane-3-carboxamide), FEMA 3455; WS-5 [Ethyl 3-(p-menthane-3-carboxamido)acetate], FEMA 4309; WS-12 (1R,2S,5R)—N-(4-Methoxyphenyl)-p-menthanecarboxamide, FEMA 4681; WS-27 (N-Ethyl-2,2-diisopropylbutanamide), FEMA 4557; N-Cyclopropyl-5-methyl-2-isopropylcyclohexanecarboxamide, FEMA 4693, WS-116 (N-(1,1-Dimethyl-2-hydroxyethyl)-2,2-diethylbutanamide), N-(1,1-Dimethyl-2-hydroxyethyl)2,2-diethylbutanamide, FEMA 4603, Menthoxyethanol, FEMA 4154, N-(4-cyanomethylphenyl)-p-menthanecarboxamide, FEMA 4496; N-(2-(Pyridin-2-yl) ethyl)-3-p-menthanecarboxamide, FEMA 4549; N-(2-Hydroxyethyl)-2-isopropyl-2,3-dimethylbutanamide, FEMA 4602 and (also N-(4-(carbamoylmethyl)phenyl)-menthylcarboxamide, FEMA 4684; (1R,2S,5R)—N-(4-Methoxyphenyl)-p-menthanecarboxamide (WS-12), FEMA 4681; (2S,5R)—N-[4-(2-Amino-2-oxoethyl)phenyl]-p-menthanecarboxamide, FEMA 4684; and N-Cyclopropyl-5-methyl-2-isopropylcyclohexanecarbonecarboxamide, FEMA 4693; 2-[(2-p-Menthoxy)ethoxy]ethanol, FEMA 4718; (2,6-Diethyl-5-isopropyl-2-methyltetrahydropyran, FEMA 4680); trans-4-tert-Butylcyclohexanol, FEMA 4724; 2-(p-tolyloxy)-N-(1H-pyrazol-5-yl)-N-((thiophen-2-yl)methyl)acetamide, FEMA 4809; Menthone glycerol ketal, FEMA 3807; menthone glyceryl ketal (FEMA GRAS 3808); (−)-Menthoxypropane-1,2-diol; 3-(1-Menthoxy)-2-methylpropane-1,2-diol, FEMA 3849; Isopulegol; (+)-cis & (−)-trans p-Menthane-3,8-diol, Ratio~62:38, FEMA 4053; 2,3-dihydroxy-p-menthane; 3,3,5-trimethylcyclohexanone glycerol ketal; menthyl pyrrolidone carboxylate; (1R,3R,4S)-3-menthyl-3,6-dioxaheptanoate; (1R,2S,5R)-3-menthyl methoxyacetate; (1R,2S,5R)-3-menthyl 3,6,9-trioxadecanoate; (1R,2S,5R)-3-menthyl 3.6,9-trioxadecanoate; (1R,2S,5R)-3-menthyl (2-hydroxyethoxy)acetate; (1R,2S,5R)-menthyl 11-hydroxy-3,6,9-trioxaundecanoate; Cubebol, FEMA 4497; N-(4-cyanomethylphenyl) p-menthanecarboxamide, FEMA 4496; 2-isopropyl-5-methylcyclohexyl 4-(dimethylamino)-4-oxobutanoate, FEMA 4230; N-(4-cyanomethylphenyl) p-menthanecarboxamide, FEMA 4496; N-(2-pyridin-2-ylethyl) p-; menthanecarboxamide, FEMA 4549, Menthyl lactate, FEMA 3748; 6-isopropyl-3,9-dimethyl-1,4-dioxaspiro[4.5]decan-2-one, FEMA 4285; N-benzo[1,3]dioxol-5-yl-3-p-menthanecarboxamide; N-(1-isopropyl-1,2-dimethylpropyl)-1,3-benzodioxole-5-carboxamide; N—(R)-2-oxotetrahydrofuran-3-yl-(1R,2S,5R)-p-menthane-3-carboxamide; mixture of 2,2,5,6,6-pentamethyl-2,3,6,6a-tetrahydropentalen-3a(1H)-ol and 5-(2-hydroxy-2-methylpropyl)-3,4,4-trimethylcyclopent-2-en-1-one; (1R,2S,5R)-2-isopropyl-5-methyl-N-(2-(pyridin-2-yl)ethyl) cyclohexanecarboxamide, FEMA 4549; (2S,5R)-2-isopropyl-5-methyl-N-(2-(pyridin-4-yl)ethyl) cyclohexanecarboxamide; N-(4-cyanomethylphenyl) p-menthanecarboxamide, FEMA 4496; (1S,2S,5R)—N-(4-(cyanomethyl)phenyl)-2-isopropyl-5-methylcyclohexanecarboxamide; 1/7-isopropyl-4/5-methyl-bicyclo[2.2.2]oct-5-ene derivatives; 4-methoxy-N-phenyl-N-[2-(pyridin-2-yl) ethyl]benzamide; 4-methoxy-N-phenyl-N-[2-(pyridin-2-yl) ethyl]benzenesulfonamide; 4-chloro-N-phenyl-N-[2-(pyridin-2-yl)ethyl]benzenesulfonamide; 4-cyano-N-phenyl-N-[2-(pyridin-2-yl)ethyl]benzenesulfonamid; 4-((benzhydrylamino)methyl)-2-methoxyphenol; 4-((bis(4-methoxyphenyl)-methylamino)-methyl)-2-methoxyphenol; 4-((1,2-diphenylethylamino)methyl)-2-methoxyphenol; 4-((benzhydryloxy)methyl)-2-methoxyphenol, 4-((9H-fluoren-9-ylamino)methyl)-2-methoxyphenol; 4-((benzhydrylamino)methyl)-2-ethoxyphenol; 1-(4-methoxyphenyl)-2-(1-methyl-1H-benzo[d]imidazol-2-yl)vinyl4-methoxybenzoate; 2-(1-isopropyl-6-methyl-1H-benzo[d]imidazol-2-yl)-1-(4-methoxyphenyl)vinyl4-methoxybenzoate; (Z)-2-(1-isopropyl-5-methyl-1H-benzo [d]imidazol-2-yl)-1-(4-methoxy-phenyl)vinyl-4-methoxybenzoate; 3-alkyl-p-methan-3-ol derivatives; derivatives of fenchyl, D-bornyl, L-bornyl, exo-norbornyl, 2-methylisobornyl, 2-ethylfenchyl, 2-methylbornyl, cis-pinan-2-yl, verbanyl and isobornyl; menthyl oxamate derivatives; menthyl 3-oxocarboxylic acid esters; N alpha-(Menthanecarbonyl)amino acid amides; p-menthane carboxamide and WS-23 analogs; (−)-(1R,2R,4S)-dihydroumbellulol; p-menthane alkyloxy amides; cyclohexane derivatives; butone derivatives; a mixture of 3-methoxy-1-propanol and 1-methoxy-2-propanol; 1-[2-hydroxyphenyl]-4-[2-nitrophenyl-]-1,2,3,6-tetrahydropyrimidine-2-one; 4-methyl-3-(1-pyrrolidinyl)-2[5H]-furanone; and combinations thereof. Preferably, the cooling agent may be selected from the group consisting of menthol, menthol methyl ether, menthone glyceryl acetal (FEMA GRAS 3807), menthone glyceryl ketal (FEMA GRAS 3808), menthyl lactate (FEMA GRAS 3748), menthyl acetate, menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomenthyl glutamate (FEMA GRAS 4006), menthoxy-1,2-propanediol (FEMA GRAS 3784), menthoxy-2-methyl-1,2-propanediol (FEMA GRAS 3849), (1R,2S,5R)—N-(4-(cyanomethyl)phenyl)menthylcarboxamide (FEMA GRAS 4496), (1R,2S,5R)—N-(2-(pyridin-2-yl)ethyl)menthylcarboxamide (FEMA GRAS 4549), the menthane carboxylic acid esters and amides WS-3, WS-4, WS-5, WS-12, WS-14, WS-30 and mixtures thereof.

According to any one of the above embodiments, the invention's composition may comprise sweeteners. Non limited-examples of suitable sweeteners includes common saccharide sweeteners, e.g., sucrose, fructose (e.g., D-fructose), glucose (e.g., D-glucose); sweetener compositions comprising natural sugars, such as *stevia* (all types and grades), corn syrup (including high fructose corn syrup) or other syrups or sweetener concentrates derived from natural fruit and vegetable sources; semisynthetic "sugar alcohol" sweeteners such as erythritol, isomalt, lactitol, mannitol, sorbitol, xylitol, maltodextrin, glycerol, threitol, arabitol, ribitol, and dulcitol; artificial sweeteners such as miraculin, aspartame, superaspartame, saccharin, saccharin-sodium salt, acesulfame-K, cyclamate, sodium cyclamate, and alitame; other sweeteners such as trehalose, melizitose, melibiose, raffinose, palatinose, lactulose, cyclamic acid, mogroside, tagatose (e.g., D-tagatose), maltose, galactose (e.g., D-galactose), L-rhamnose, D-sorbose, maunose (e.g., D-maunose), lactose, L-arabinose, D-ribose, D-glyceraldehyde, curculin, brazzein, mogroside, Neohesperidin dihydrochalcone (NHDC), neotame and other aspartame derivatives, D-tryptophan, D-leucine, D-threonine, glycine, D-asparagine, D-phenylalanine, L-proline, maltitol, hydrogenated glucose syrup (HGS), magap, sucralose, lugduname, sucrononate, sucrooctate, monatin, phyllodulcin, hydrogenated starch hydrolyzate (HSH), stevioside, rebaudioside A, rebaudioside D, rebadioside M, and other sweet Stevia based glycosides, lo han guo, thaumatin, monellin, carrelameand and other guanidine-based sweeteners.

According to any one of the above embodiments, the flavored composition may further comprise ingredient imparting a warming, a tingling, a salivating, a cleaning or an alcohol enhancement effect such as capsicum extract, spice extract (e.g. ginger, maniguette, all types of peppers including Sichuan, piperine, capsaicine, jambu extract, spilanthol.

According to any one of the above embodiments, the invention's flavoring composition may be in the form of a confectionery such as a chewing gum, a bubblegum, a pastillage, a sugarless confectionary or a oral care product, such as, for example, a toothpaste, a mouth wash, a dental care product, a denture adhesive, a dental rinsing, a mouth spray or a dental floss.

Furthermore, the invention's composition of matter can also be advantageously used in all the fields of flavor to positively impart or modify the taste of a consumer product into which said composition of matter is added. Consequently, another object of the present invention is represented by a flavored consumer product comprising the invention's composition as defined above.

The invention's composition of matter can be added as such or as part of an invention's flavoring composition.

For the sake of clarity, by "flavored consumer product" it is meant to designate a edible product which may be food or beverage and which can be fried or not, as well as frozen or not, low fat or not, marinated, battered, chilled, dehydrated, instant, canned, reconstituted, retorted or preserved. Therefore, a flavored article according to the invention comprises the invention's composition, as well as optional benefit agents, corresponding to taste and flavor profile of the desired edible product, e.g. a savory cube.

The nature and type of the constituents of the foodstuffs or beverages do not warrant a more detailed description here, the skilled person being able to select them on the basis of his general knowledge and according to the nature of said product.

Typical examples of said flavoring consumer product include:
seasoning or condiment, such as a stock, a savory cube, a powder mix, a flavored oil, a sauce (e.g. a relish, a barbecue sauce, a dressing, a gravy or a sweet and/or a sour sauce), a salad dressing or a mayonnaise;
meat-based product, such as a poultry, beef or pork based product, a seafood, surimi, or a fish sausage;
soup, such as a clear soup, a cream soup, a chicken or beef soup or a tomato or asparagus soup;
carbohydrate-based product, such as instant noodles, rice, pasta, potatoes flakes or fried, noodles, pizza, tortillas, wraps;
dairy or fat product, such as a spread, a cheese, or regular or low fat margarine, a butter/margarine blend, a butter, a peanut butter, a shortening, a processed or flavored cheese;
savory product, such as a snack, a biscuit (e.g. chips or crisps) or an egg product, a potato/tortilla chip, a microwave popcorn, nuts, a bretzel, a rice cake, a rice cracker, etc;
confectionery, such as bakers' confectionary (e.g. a sweet pastrie or a cake), sugar confectionary (e.g. a sweet, a candy, a candied nut, a chocolate, a chewing gum and bubblegum, a sweetmeat, a pastillage, a sugarless confectionary) or chocolate confection;
oral care product, such as a toothpaste, a mouth wash, a dental care product (e.g. denture adhesive), a dental rinsing, a mouth spray, a dental powder, a dental gel or dental floss;
imitation products, such as a dairy (e.g a reformed cheese made from oils, fats and thickeners) or seafood or meat (e.g. a vegetarian meat replacer, a veggie burger) or analogues;
pet or animal food; or
beverage such as a hot drink (e.g. a tea), a soft drink including carbonated, an alcoholic drink, a ready-to-drink or a powder soft.

Particularly preferred flavored consumer products, in which the invention's composition finds utility, include confectionery and oral care, preferably oral care product.

Some of the above-mentioned flavored consumer products may represent an aggressive medium for the invention's composition of matter, so that it may be necessary to protect the latter from premature decomposition, for example by encapsulation or by chemically binding it to another chemical which is suitable to release the invention's composition of matter upon a suitable external stimulus, such as an enzyme, light, heat or a change of pH.

The proportions in which the invention's composition of matter can be incorporated into the various of the aforementioned products vary within a wide range of values. These values are dependent on the nature of the article to be flavored and on the desired organoleptic effect as well as the nature of the co-ingredients in a given base when the composition according to the invention are mixed with perfuming or flavoring ingredients, solvents or additives commonly used in the art.

For example, in the case of flavoring compositions, typical concentrations of invention's composition of matter are in the order of 0.001 ppm to 1000 ppm by weight, based on the weight of the composition into which they are incorporated. In the case of flavored consumer product, typical concentrations are in the order of 0.001 ppm to 1000 ppm by weight, more preferably 0.5 ppm to 500 ppm, most preferably 1 to 350 ppm, of the invention's composition of matter based on the weight of the consumer product into which they are incorporated.

The invention's composition of matter may also be used as a perfuming ingredient. So, the invention concerns the use of a composition comprising at least one compound of formula (I) and at least a $C_{1-6}$ linear or branched alkyl lactate as a perfuming ingredient. In other words, it concerns a method or a process to confer, enhance, improve or modify the odor properties of a perfuming composition or of a perfumed article or of a surface, which method comprises adding to said composition or article an effective amount of the invention's composition of matter, e.g. to impart its typical note.

By "use of a composition of matter" it has to be understood here also the use of any composition containing at least one compound of formula (I) and at least a $C_{1-6}$ linear or branched alkyl lactate and which can be advantageously employed in the perfumery industry.

Said compositions, which in fact can be advantageously employed as perfuming ingredients, are also an object of the present invention.

Therefore, another object of the present invention is a perfuming composition comprising:
i) at least a composition of matter comprising at least one compound of formula (I) and at least a $C_{1-6}$ linear or branched alkyl lactate, as defined above;
ii) at least one ingredient selected from the group consisting of a perfumery carrier, a perfuming co-ingredient and a mixture thereof; and
iii) optionally at least one perfumery adjuvant.

By "perfumery carrier" it is meant here a material which is practically neutral from a perfumery point of view; i.e. which does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfuming co-ingredients, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. BOne et al. Chimia, 2011, vol. 65, pages 177-181.

By "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor. Said perfuming co-ingredient is not of formula (I).

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite as perfuming co-ingredients which are commonly used in perfume formulations:
Aldehydic ingredients: decanal, dodecanal, 2-methyl-undecanal, 10-undecenal, octanal and/or nonenal;
Aromatic-herbal ingredients: eucalyptus oil, camphor, eucalyptol, menthol and/or alpha-pinene;
Balsamic ingredients: coumarine, ethylvanillin and/or vanillin;
Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;
Floral ingredients:Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4 (2H)-pyranol, beta ionone, methyl 2-(methylamino) benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethyl-propoxy)propanoate, 2-methoxynaphthalene, 2,2,2-trichloro-1-phenylethyl acetate, 4/3-(4-hydroxy-4-methylpentyl)-3-cyclohexene-1-carbaldehyde,
amylcinnamic aldehyde, 4-phenyl-2-butanone, isononyle acetate, 4-(1,1-diméthyléthyl)-1-cyclohexyl acetate, verdyl isobutyrate and/or mixture of methyl-ionones isomers;
Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;
Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;
Musk ingredients: 1,4-dioxa-5,17-cycloheptadecane-dione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;
Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2, 2,3-trimethyl-3-cyclopenten-1-yl)-2-buten-1-ol,
Methyl cedryl ketone, 5-(2,2,3-trimethyl-3-cyclopentenyl)-3-methylpentan-2-ol, 1-(2,3,8,8-tetramethyl-1,2,3, 4,6,7,8,8a-octahydronaphthalen-2-yl)ethan-1-one and/or isobornyl acetate;
Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1, 3-benzodioxol-5-yl)-2-methylpropanal and/or 3-(3-isopropyl-1-phenyl)butanal.

A perfuming co-ingredients according to the invention may not be limited to the above mentioned ones, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I), at least a $C_{1-6}$ linear or branched alkyl lactate and at least one perfumery carrier consists of a particular embodiment of the invention as well as a perfuming composition comprising at least one compound of formula (I), at least a $C_{1-6}$ linear or branched alkyl lactate, at least one perfumery carrier, at least one perfuming co-ingredient, and optionally at least one perfumery adjuvant.

According to any one of the above embodiments, the invention's perfuming composition may be in the form of a a shampoo, a coloring preparation, a hair spray, a color-care product, a hair shaping product, a dental care product, a disinfectant, an intimate care product, a skin cream or lotion, a vanishing cream, a deodorant or antiperspirant, a hair remover, a tanning or sun product, a nail product, a skin cleansing, a makeup, a perfumed soap, a shower or bath mousse, an oil or gel, a foot/hand care product, a hygiene product, an air freshener, a "ready to use" powdered air freshener, a mold remover, furnisher care, a wipe, a dish detergent or a hard-surface detergent, a leather care product. Preferably, the invention's perfuming composition may be in the form an air freshener.

Furthermore, the invention's composition of matter can also be advantageously used in all the fields of modern perfumery, i.e. fine or functional perfumery, to positively impart or modify the odor of a consumer product into which said compound (I) is added. Consequently, another object of the present invention is represented by a perfumed consumer product comprising the invention's composition of matter as defined above.

The invention's composition of matter can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's composition of matter, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the invention's composition of matter can be incorporated into the various of the aforementioned products vary within a wide range of values. These values are dependent on the nature of the article to be perfumed and on the desired organoleptic effect as well as the nature of the co-ingredients in a given base when the composition of matter according to the invention are mixed with perfuming ingredients, solvents or additives commonly used in the art.

For example, in the case of perfuming compositions, typical concentrations are in the order of 0.001 ppm to 1000 ppm by weight, or even more, of the invention's composition of matter based on the weight of the composition into which they are incorporated. In the case of perfumed consumer product, typical concentrations are in the order of 0.01 ppm to 500 ppm by weight, or even more, of the invention's composition of matter based on the weight of the consumer product into which they are incorporated.

Another object of the present invention is a process for preparing the composition of matter as defined above comprising the step of
a) preparing compound of formula (I) as defined in claim 1 by reacting a compound of formula

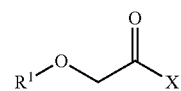

(II)

wherein $R^1$ represents a phenyl group optionally substituted by one or two $C_{1-3}$ alkyl or alkoxy groups or by one or two halide groups; and X represents a hydroxyl group, a $C_{1-10}$ alkoxy group or a chloride atom;
with a compound of formula

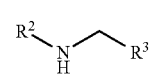

(III)

wherein $R^2$ and $R^3$ represent, independently from each other a heterocyclic group comprising from 1 to 3 heteroatoms selected from nitrogen, oxygen and sulfur, optionally substituted by one or two $C_{1-3}$ alkyl groups;

b) crystallizing the reaction mixture obtained in step a);
c) filtering the solution of the crystallized product obtained in step b);
d) drying the crystallized product obtained in step c); and
e) solubilizing the dried crystallized product obtained in step d) in a $C_{1-6}$ linear or branched alkyl lactate.

For the sake of clarity, by the term "crystallizing" it is meant the normal meaning in the art; i.e. the reaction mixture is put under conditions in order to favor the growing of the crystals.

According to any one of the above embodiment, $R^1$, $R^2$ and $R^3$ have the same meaning as defined above.

According to any one of the above embodiment, the step a) is an amidation reaction. The person skilled in the art is well aware of the conditions to apply in order to obtain the desired product. Non-limiting examples of suitable reagents/conditions in order to carry out step a) include thermal conditions, the presence of a base or a Lewis acid. The choice of the reaction conditions is a function of the nature of the substrate and the person skilled in the art is well able to select conditions most convenient in each case to optimize the reaction. Preferably, the step a) is performed in the presence of a base or under thermal conditions by heating the reaction mixture at a temperature above 150° C. Even more preferably, the step a) is performed in the presence of a base. Non-limiting examples of suitable base include amine base such as pyridine, trimethylamine, lutidine, N,N-Diisopropylethylamine or 1,8-Diazabicyclo[5.4.0]undec-7-ene or alkali metal alkoxide, carbonate or hydroxide. Preferably, the base may be an alkali metal alkoxide, carbonate or hydroxide. Even more preferably, base may be an alkali metal alkoxide. Even more preferably, base may be sodium or potassium methoxide ethoxide, propoxide, butoxide or tert-butoxide. Even more preferably, base may be sodium or potassium methoxide.

According to any one of the above embodiment, X represents a $C_{1-10}$ alkoxy group. Preferably, X may represent a $C_{1-5}$ alkoxy group. Even more preferably, X may represent a $C_{1-3}$ alkoxy group. Even more preferably, X may be a methoxy, an ethoxy or a propoxy group, even more an ethoxy group.

Compound of formula (II) and (III) may be prepared according to a method known in the art or as reported in WO 2012/061698.

The step a) can be carried out in the presence or absence of a solvent. When a solvent is required or used for practical reasons, then any solvent current in such reaction type can be used for the purposes of the invention. Non-limiting examples include methanol, ethanol, cyclohexane, THF, Me-THF, MTBE, DME, $Et_2O$, toluene, butanone, dichloromethane, dodecane. The choice of the solvent is a function of the nature of the compound of formula (II) and (III) and/or the base and the person skilled in the art is well able to select the solvent most convenient in each case to optimize the reaction.

According to any one of the invention's embodiments, the invention's process is carried out at a temperature comprised between 20° C. and 250° C. In particular, the temperature is in the range between 30° C. and 150° C. Of course, a person skilled in the art is also able to select the preferred temperature as a function of the melting and boiling point of the starting and final products as well as the desired time of reaction or conversion.

According to any one of the above embodiment, the crystallization of step b) is carried out by slowly cooling the reaction mixture at room temperature over a period of more than 5 hours, preferably more than 10 hours.

According to any one of the above embodiment, steps c) to e) of the invention's process are performed in the same equipment; i.e. an Agitated Filter Dryer also known as a Nucha Vacuum Filter-Dryer, a Filter-dryer or an Agitated Nutsche Filter Dryer. Filtering, drying and solubilizing in the same equipment allows reducing the handling of the obtained compound of formula (I).

The compound of formula (I) obtainable by performing step a) to d) is in a form of a crystal. Surprisingly, it has been discovered that compound of formula (I) can crystallize in more than one type of three-dimensional crystal structure. In other word, several polymorphs of compound of formula (I), and in particular N-(1H-pyrazol-3-yl)-N-(thiophen-2-ylmethyl)-2-(p-tolyloxy)acetamide, have been obtained. It is well known that Polymorphs of a particular organic compound may have different physical properties, such as solubility and hygroscopicity, due to their distinct three-dimensional crystal structures. However, it is generally not possible to predict whether a particular organic compound will form different crystalline forms, let alone predict the structure and properties of the crystalline forms themselves. The discovery of a new crystalline or polymorph form of a useful compound may provide a new opportunity for improving the overall characteristics of an end product such as a flavored or perfumed consumer product. It enlarges the repertoire of materials that a formulation scientist has available for designing. It may be advantageous when this repertoire is enlarged by the discovery of new polymorphs of a useful compound. The most stable polymorph of compound N-(1H-pyrazol-3-yl)-N-(thiophen-2-ylmethyl)-2-(p-tolyloxy)acetamide has been obtained following the invention's process. So another object of the invention is a crystalline form of N-(1H-pyrazol-3-yl)-N-(thiophen-2-ylmethyl)-2-(p-tolyloxy)acetamide, characterized by main peaks in its powder X-ray diffraction pattern obtained using copper K-alpha, radiation at 6.86, 12.46, 15.87, 17.38, 17.70, 17.93, 18.43, 19.46, 20.61, 22.08, 23.03, 23.43, 24.36, 26.11, 27.59, 34.68. The invention's composition of matter can be prepared according to a method as described herein-below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of the Invention Composition of Matter a) Preparation of a Composition of Matter Comprising N-(1H-pyrazol-3-yl)-N-(thiophen-2-ylmethyl)-2-(p-tolyloxy)acetamide and ethyl lactate A 1.5 l, five-necked flask equipped with a temperature probe, a reflux condenser with a nitrogen inlet, a septum, a mechanical stirrer and a stopper was charged with N-(thiophen-2-ylmethyl)-1H-pyrazol-5-amine (58 g, 0.324 mol), 51 g absolute ethanol and ethyl 2-(p-tolyloxy)acetate (72.5 g, 0.373 mol). Sodium methoxide (67 g of a 30% solution in methanol, 0.372 mol) was added and the reaction mixture heated at 55° C. for 7 h. The reaction mixture was diluted with ethanol (297 g) and the temperature brought to 50° C. The pH was adjusted to 11.7 by the addition of 25% citric acid aqueous solution (60.7 g). Water (487 g) was added over 15 min and the resulting suspension heated to 68° C. Slow cooling of the crude solution to 15° C. was followed by filtration and washing of the solids twice with 131 g of a solution containing 1 part ethanol and 2 parts water. The solids were then washed with demineralised water (176 g) and dried under reduced pressure to give N-(1H-pyrazol-3-yl)-N-(thiophen-2-ylmethyl)-2-(p-tolyloxy)acetamide as a colourless solid (74.19 g, 0.227 mol). This solid is then diluted in ethyl lactate (456 g) to provide a composition comprising 14% of N-(1H-pyrazol-3-yl)-N-(thiophen-2-ylmethyl)-2-(p-tolyloxy)acetamide and 86% of ethyl lactate.

b) Preparation of a composition of matter comprising 2-(4-ethylphenoxy)-N-(1H-pyrazol-3-yl)-N-(thiophen-2-ylmethyl)acetamide and ethyl lactate A 350 ml, five-necked flask equipped with a temperature probe, a reflux condenser with a nitrogen inlet, a septum, a mechanical stirrer and a stopper was charged with N-(thiophen-2-ylmethyl)-1H-pyrazol-5-amine (9.50 g, 53.0 mmol), 8.71 g absolute ethanol and ethyl 2-(4-ethylphenoxy)acetate (11.81 g, 60.8 mmol). Sodium methoxide (10.86 g of a 30% solution in methanol, 60.3 mmol) was added and the reaction mixture heated at 55° C. for 7 h. The reaction mixture was diluted with ethanol (49.4 g) and the temperature brought to 55° C. The pH was adjusted to 10.9 by the addition of 25% citric acid aqueous solution (10.24 g) and Water (80.0 g). The resulting suspension was heated to 70° C. Slow cooling of the crude solution to 19° C. was followed by filtration and washing of the solids twice with 42.9 g of a solution containing 1 part ethanol and 2 parts water. The solids were then washed with demineralised water (121 g) and dried under reduced pressure to give 2-(4-ethylphenoxy)-N-(1H-pyrazol-3-yl)-N-(thiophen-2-ylmethyl)acetamide as a colourless solid (12.96 g, 36.9 mmol). This solid is then diluted in ethyl lactate (246 g) to provide a composition comprising 5% of N-(1H-pyrazol-3-yl)-N-(thiophen-2-ylmethyl)-2-(p-tolyloxy)acetamide and 95% of ethyl lactate.

The analytically pure material was obtained by recrystallization of the solid from ethanol.

Example 2

Solubility of Compound of Formula (I)

A precise amount of the powder was weighed into a transparent 8 mL tube, 3 g of solvent was added, and the tube was sealed with a cap equipped with an integrated overhead stirrer. The tube was immediately transferred to a Crystalline PV instrument (Technobis Crystallization Systems, The Netherlands), and placed into a precooled reactor at 3° C. The sample was heated and stirred in the reactor at a rate of 0.1° C./min up to 60° C. Each reactor of the Crystalline PV instrument is equipped with an LED sensor and a digital camera, and data is acquired as real-time transmittance to detect turbidity or as video images for visualization. The solubility temperature is reached when all particles have dissolved. In order to establish a temperature solubility curve, at least 4 samples with different concentrations are measured. The data are fitted to an exponential curve according to the model of Hoffmann, and solubility as a function of temperature can be calculated by extrapolation. Under this method, the solubility of N-(1H-pyrazol-3-yl)-N-(thiophen-2-ylmethyl)-2-(p-tolyloxy)acetamide in different solvents, which could be used in flavor application, was measured. The results are reported in Table 1.

TABLE 1

Measure of the solubility of N-(1H-pyrazol-3-yl)-N-(thiophen-2-ylmethyl)-2-(p-tolyloxy)acetamide in different solvents

| Solubility | 22° C. |
|---|---|
| Mint *piperita* | 2.1% |
| Ethanol abs. | 3.3% |
| PG | 0.4% |
| triacetin | 1.2% |
| Ethyl lactate | 8.6% |
| triethyl citrate | 3.1% |
| Dowanol TPM | 5.4% |
| Augeo Clean Multi | 5.7% |

The solubility of N-(1H-pyrazol-3-yl)-N-(thiophen-2-ylmethyl)-2-(4-ethylphenoxy)acetamide in the solvent ethyl lactate in ethyl lactate at 22° C. was found to be 26.1%.

Example 3

Analysis of Polymorph of N-(1H-pyrazol-3-yl)-N-(thiophen-2-ylmethyl)-2-(p-tolyloxy)acetamide obtained following experimental part of example 1 a) 13C Solid State NMR Spectroscopy

The sample was finely ground and filled into a 4 mm ZrO2 rotor. A 13C solid state NMR spectrum was recorded on a Bruker AVII 400 MHz spectrometer equipped with a CPMAS probe head. The sample was spun at 4000 Hz at room temperature. A pulse sequence for the total suppression of side bands (CPTOSS) with a cross polarization ramp of 2 ms was run, and 10 k scans were accumulated. The spectrum was transformed using a line broadening function of 20 Hz.

Peaks: (δ in ppm vs. external standard adamantane): 170.33, 156.04, 147.10, 143.55, 131.18, 129.04, 126.57, 125.31, 98.34, 66.48, 48.91, 21.75.

b) X-Ray Powder Diffraction

The powder sample was finely ground and filled into a disk sample holder.

Diffractograms were acquired on a PANalytical Empyrean powder diffractometer with Kα1 monochromator in reflection mode. The 2 theta scanning range was between 3 and 80°.

Crystalline form of the compound characterized by main peaks in its powder X-ray diffraction pattern (degree 2-theta): 6.86, 12.46, 15.87, 17.38, 17.70, 17.93, 18.43, 19.46, 20.61, 22.08, 23.03, 23.43, 24.36, 26.11, 27.59, 34.68.

The molecules are arranged within a P21/c space group with one molecule per unit cell.

Example 4

Preparation of a Flavoring Composition Comprising an Invention's Composition of Matter A flavoring composition imparting a green floral note was prepared by admixing the following ingredients:

TABLE 2

Flavoring composition

| Ingredient | Parts by Weight |
| --- | --- |
| Mint *Arvensis* Terpeneless | 520 |
| Anethol | 911 |
| 4-Decanolide | 20 |
| Eucapyptol | 155 |
| *Eucalyptus Globulus* | 250 |
| 2-methoxy-4-(2-propen-1-yl)phenol | 84 |
| 10%* N-(1H-pyrazol-3-y1)-N-(thiophen-2-ylmethyl)-2-(p-tolyloxy) acetamide | 148 |
| Allyl heptanoate | 30 |
| Peppermint oil Brazil | 808 |
| Teton mint | 95 |
| Menthol melted | 4738 |
| Mint *piperita* oil Hybrid | 1420 |
| Hedione ®[1)] | 10 |
| 4-Octanolide | 48 |
| Peppermint USA Cascade oil | 625 |
| (+−)-(3E)-4-(2,6,6-trimethyl-2-cyclohexen-1-yl)-3-buten-2-one | 38 |
| (1R,2S,5R)-N-ethyl-2-isopropyl-5-methylcyclohexanecarboxamide | 100 |
| Total | 10000 |

* in Ethyl lactate
[1)]methyl 2-((1RS,2RS)-3-oxo-2-pentylcyclopentyl)acetate; origin: Firmenich SA, Geneva, Switzerland This flavoring composition may be added to an oral care product or to confectionary such as chewing-gum.

Example 5

Preparation of a Flavoring Composition Comprising an Invention's Composition of Matter A flavoring composition imparting a spearmint note was prepared by admixing the following ingredients:

TABLE 3 flavoring composition

| Ingredient | Parts by Weight |
| --- | --- |
| Anethol | 930 |
| (−)-2-methyl-5-(1-propen-2-yl)-2-cyclohexen-1-one | 880 |
| 10%* N-(1H-pyrazol-3-y1)-N-(thiophen-2-ylmethyl)-2-(p-tolyloxy) acetamide | 90 |
| Mint *Spicata* | 1040 |
| Mint *arvensis* Terpeneless | 650 |
| Menthol melted | 3280 |
| Mint *piperita* oil Hybrid | 250 |
| Linseed oil | 1190 |
| Mint *Piperita* Rectified India | 680 |
| Mint *Spicata* oil | 910 |
| (1R,2S,5R)-N-ethyl-2-isopropyl-5-methylcyclohexanecarboxamide | 100 |
| Total | 10000 |

*in Ethyl lactate

This flavoring composition may be added to an oral care product or to confectionary such as chewing-gum.

The invention claimed is:

1. A composition comprising:
i) from 0.1 wt % to 20 wt %, relative to the total weight of the composition, of at least one compound selected from the group consisting of N-(1H-pyrazol-5-yl)-N-(thiophen-2-ylmethyl)-2-(p-tolyloxy)acetamide, N-(1H-pyrazol-3-yl)-N-(thiophen-2-ylmethyl)-2-(p-tolyloxy)acetamide, 2-(4-ethylphenoxy)-N-(1H-pyrazol-5-yl)-N-(thiophen-2-ylmethyl)acetamide and 2-(4-ethylphenoxy)-N-(1H-pyrazol-3-yl)-N-(thiophen-2-ylmethyl)acetamide; and
ii) from 80 wt % to 99.9 wt %, relative to the total weight of the composition, of ethyl lactate.

2. A process for preparing a composition comprising
i) at least one compound of formula (I)

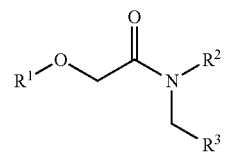

(I)

in the form of any of its stereoisomers; and wherein $R^1$ represents a phenyl group optionally substituted by one or two $C_{1-3}$ alkyl or alkoxy groups or by one or two halide groups; $R^2$ and $R^3$ represent, independently from each other a heterocyclic group comprising from 1 to 3 heteroatoms selected from nitrogen, oxygen and sulfur, optionally substituted by one or two $C_{1-3}$ alkyl groups; and
ii) at least a $C_{1-6}$ linear or branched alkyl lactate;
the process comprising the steps of
a) preparing the at least one compound of formula (I) by reacting a compound of formula

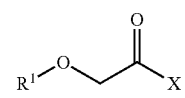

(II)

wherein $R^1$ has the same meaning as defined above; and X represents a hydroxyl group, a $C_{1-10}$ alkoxy group or a chloride atom;
with a compound of formula

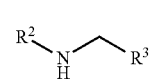

(III)

wherein $R^2$ and $R^3$ each have the same meaning as defined above;
b) crystallizing the reaction mixture obtained in step a);
c) filtering the solution of the crystallized product obtained in step b);
d) drying the crystallized product obtained in step c); and
e) solubilizing the dried crystallized product obtained in step d) in the $C_{1-6}$ linear or branched alkyl lactate.

3. The process according to claim 2, characterized in that X represents a $C_{1-5}$ alkoxy group.

4. The process according to claim 2, characterized in that the step a) is carried out in the presence of a base.

5. The process according to claim 4, characterized in that the base is an alkali metal alkoxide, carbonate or hydroxide.

6. The process according to claim 2, characterized in that the steps c) to e) of the process are performed in the same equipment.

7. A crystalline form of N-(1H-pyrazol-3-yl)-N-(thiophen-2-ylmethyl)-2-(p-tolyloxy)acetamide characterized by main peaks in its powder X-ray diffraction pattern obtained using copper K-alpha, radiation at 6.86, 12.46, 15.87, 17.38, 17.70, 17.93, 18.43, 19.46, 20.61, 22.08, 23.03, 23.43, 24.36, 26.11, 27.59, and 34.68.

8. The process according to claim 2, characterized in that $R^1$ represents a phenyl group substituted by one or two $C_{1-3}$ alkyl or alkoxy groups or by one or two halide groups.

9. The process according to claim 2, characterized in that $R^1$ represents a phenyl group substituted by one or two $C_{1-2}$ alkyl or alkoxy groups or by one or two fluoro groups.

10. The process according to claim 2, characterized in that $R^1$ represents a phenyl group substituted by one or two methyl, ethyl, or methoxy groups or by one fluoro group.

11. The process according to claim 2, characterized in that $R^2$ and $R^3$ represent, independently from each other a heterocyclic group comprising from 1 to 3 heteroatoms selected from nitrogen and sulfur.

12. The process according to claim 2, characterized in that $R^2$ represents a heterocyclic group comprising from one to two nitrogen atoms.

13. The process according to claim 2, characterized in that $R^2$ represents a pyrazolyl group.

14. The process according to claim 2, characterized in that $R^3$ represents a heterocyclic group comprising from one to two sulfur atoms.

15. The process according to claim 2, characterized in that $R^3$ represents a thiophenyl group.

16. The process according to claim 2, characterized in that the $C_{1-6}$ linear or branched alkyl lactate is ethyl lactate.

17. The composition according to claim 1, characterized in that the composition comprises from 0.5 wt % to 15 wt % of the at least one compound, relative to the total weight of the composition and from 85 wt % to 99.5 wt % of the ethyl lactate, relative to the total weight of the composition.

18. The process according to claim 2, characterized in that the compound of formula (I) is N-(1H-pyrazol-5-yl)-N-(thiophen-2-ylmethyl)-2-(p-tolyloxy)acetamide, N-(1H-pyrazol-3-yl)-N-(thiophen-2-ylmethyl)-2-(p-tolyloxy)acetamide, 2-(4-ethylphenoxy)-N-(1H-pyrazol-5-yl)-N-(thiophen-2-ylmethyl)acetamide or 2-(4-ethylphenoxy)-N-(1H-pyrazol-3-yl)-N-(thiophen-2-ylmethyl)acetamide.

19. A flavoring composition comprising:
  i) the composition as defined in claim 1;
  ii) at least one ingredient selected from the group consisting of a flavor carrier, a flavoring co-ingredient and a mixture thereof; and
  iii) optionally at least one flavor adjuvant.

20. The flavoring composition according to claim 19, characterized in that the composition comprises at least one cooling agent.

21. The flavoring composition according to claim 20, characterized in that the cooling agent is selected from the group consisting of menthol, menthol methyl ether, menthone glyceryl acetal (FEMA GRAS' 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomethyl glutamate (FEMA GRAS 4006), menthoxy-1,2-propanediol (FEMA GRAS 3784), menthoxy-2-methyl-1,2-propanediol (FEMA GRAS 3849), (1R,2S,5R)—N-(4-(cyanomethyl)phenyl)menthylcarboxamide (FEMA GRAS 4496), (1R,2S,5R)—N-(2-(pyridin-2-yl)ethyl)menthylcarboxamide (FEMA GRAS 4549), menthane carboxylic acid esters and amides WS-3, WS-4, WS-5, WS-12, WS-14, WS-23 (2-Isopropyl-N,2,3-trimethylbutyramide, FEMA GRAS 3804), WS-30, and mixtures thereof.

22. A flavored consumer product comprising the composition as defined in claim 1.

23. The flavored consumer product according to claim 22, characterized in that the flavored consumer product is a seasoning, a condiment, a meat-based product, a soup, a carbohydrate-based product, a dairy or fat product, a savory product, a confectionery, an oral care product, an imitation product, a pet or animal food, or a beverage.

24. The flavored consumer product according to claim 23, characterized in that the flavored consumer product is a stock, a savory cube, a powder mix, a flavored oil, a sauce, a relish sauce, a barbecue sauce, a dressing sauce, a gravy sauce, a sweet sauce, a sour sauce, a salad dressing or a mayonnaise, a poultry, a beef or pork based product, a seafood, a surimi, a fish sausage, a clear soup, a cream soup, a chicken or beef soup or a tomato or asparagus soup, an instant noodle, rice, pasta, a potatoes flake or fried, a pizza, a tortilla, a wrap, a noodle, a spread, a cheese, a regular or low fat margarine, a butter/margarine blend, a butter, a peanut butter, a shortening, a processed or flavored cheese, a snack, a biscuit, a chip, a crisp, an egg product, a potato/tortilla chip, a microwave popcorn, a nut, a bretzel, a rice cake, a rice cracker, an imitation dairy, an imitation seafood, an imitation meat, a pet or animal food, a ready-to-drink beverage, a powder soft beverage, a hot drink, a tea, a soft drink, a carbonated soft drink, an alcoholic drink, a ready-to-drink or a powder soft, bakers' confectionary, a sweet pastry, a cake, a sugar confectionary, a sweet, a candy, a candied nut, a chocolate, a chewing gum, a bubblegum, a sweetmeat, a pastillage, a sugarless confectionary, a chocolate confection, a toothpaste, a mouth wash, a dental care product, a denture adhesive, a dental rinsing, a mouth spray or a dental floss.

25. A perfuming composition comprising:
  i) the composition as defined in claim 1;
  ii) at least one ingredient selected from the group consisting of a perfumery carrier, a perfuming co-ingredient and a mixture thereof; and
  iii) optionally at least one perfumery adjuvant.

26. A perfumed consumer product comprising the composition as defined in claim 1.

27. The perfumed consumer product according to claim 26, characterized in that the perfumed consumer product is a perfume, a fabric care product, a body-care product, a cosmetic preparation, a skin-care product, an air care product or a home care product.

28. The perfumed consumer product according to claim 27, characterized in the perfumed consumer product is a fine perfume, a splash or eau de parfum, a cologne, a shave or after-shave lotion, a liquid or a solid detergent, a fabric softener, a liquid or solid scent booster, a fabric refresher, an ironing water, a paper, a bleach, a carpet cleaner, a curtaing care product, a shampoo, a coloring preparation, a hair spray, a color-care product, a hair shaping product, a dental care product, a disinfectant, an intimate care product, a skin cream or lotion, a vanishing cream, a deodorant or antiperspirant, a hair remover, a tanning or sun product, a nail product, a skin cleansing, a makeup, a perfumed soap, a shower or bath mousse, an oil or gel, a foot/hand care product, a hygiene product, an air freshener, a "ready to use" powdered air freshener, a mold remover, furnisher care, a wipe, a dish detergent or a hard-surface detergent, a leather care product, or a car care product.

29. A method to confer, improve or modify the taste properties of a flavoring composition or of a flavored article or of a surface, which method comprises adding to said composition or article or surface an effective amount of the composition as defined in claim 1.

30. A method to confer, improve or modify the odor properties of a perfuming composition or of a perfumed article or of a surface, which method comprises adding to said composition or article or surface an effective amount of the composition as defined in claim 1.

* * * * *